United States Patent
Halalay et al.

(10) Patent No.: US 8,082,776 B2
(45) Date of Patent: Dec. 27, 2011

(54) ON-VEHICLE EVALUATION OF OIL FORMULATION

(75) Inventors: Ion C. Halalay, Grosse Pointe Park, MI (US); Eric W. Schneider, Shelby Township, MI (US); Robert M. Olree, Troy, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 379 days.

(21) Appl. No.: 12/471,598

(22) Filed: May 26, 2009

(65) Prior Publication Data
US 2010/0300188 A1 Dec. 2, 2010

(51) Int. Cl.
*G01M 15/00* (2006.01)
(52) U.S. Cl. .................. 73/114.55; 73/10; 73/53.05
(58) Field of Classification Search ........... 73/10, 53.05, 73/53.06, 54.01, 54.02, 114.55, 114.56
See application file for complete search history.

(56) References Cited

U.S. PATENT DOCUMENTS

| | | | |
|---|---|---|---|
| 4,845,469 A * | 7/1989 | Benda | 340/450.3 |
| 6,922,064 B2 | 7/2005 | Halalay et al. | |
| 7,362,110 B2 | 4/2008 | Halalay et al. | |
| 7,370,514 B2 | 5/2008 | Halalay et al. | |
| 7,835,875 B2 * | 11/2010 | Halalay et al. | 702/50 |
| 7,940,060 B2 * | 5/2011 | Halalay et al. | 324/698 |
| 2002/0162385 A1 * | 11/2002 | Ismail et al. | 73/53.05 |
| 2006/0232267 A1 * | 10/2006 | Halalay et al. | 324/158.1 |
| 2010/0250156 A1 * | 9/2010 | Halalay et al. | 702/50 |

* cited by examiner

*Primary Examiner* — Eric S McCall
(74) *Attorney, Agent, or Firm* — Reising Ethington P.C.

(57) ABSTRACT

This invention is a method for determining the quality of lubrication oil added to a quantity of used oil in an operating engine or mechanism such as occurs during an oil change or when additional oil is added to maintain the vehicle manufacturer's specified total volume of oil. The method is based on identifying the electrical resistivity characteristics of the oil addition, representative of both the base oil formulation and its additive package, and, through comparison with previously-generated resistivity data on multiple oils identifying the oil addition. The added oil may then be compared with manufacturer specifications for the specific application to determine whether it meets recommended manufacturer requirements.

23 Claims, 3 Drawing Sheets

ON-VEHICLE EVALUATION OF OIL FORMULATION

TECHNICAL FIELD

This invention relates to using electrical measurements of the resistivity of engine lubricant, which may comprise a mixture of used and unused oils, to identify and assess the quality of the oil. A particular aspect of the invention is to determine the quality of an unused oil after it is added to and commingled with used oil such as occurs during an oil change or when additional oil is added to maintain the vehicle manufacturer's specified total volume of oil.

BACKGROUND OF THE INVENTION

Oils are generally complex mixtures of chemical compounds characterized by a base stock and a combination of additives, collectively described as an additive package, selected to improve specific performance attributes. Both the base stock and the additive package are generally specific to a particular application and intended use and convey desired oil attributes at a level commensurate with the oil's intended application.

In a typical vehicle engine lubricating oil is pumped from a sump over and through the moving parts of the internal combustion engine. The oil is heated incidental to the combustion process and cooled to maintain a suitable operating temperature, often in the range of about 90° C. to about 110° C. An oil of specified quality grade is charged to the engine and its properties deteriorate with usage. The specified oil and any suitable equivalents have known or determined electrical resistivity properties obtained over their operating life in like engines (or other lubricated mechanisms).

Associated with the engine is a computer-based engine control system. In accordance with this invention, data for the practice of this invention is maintained and processed in such a computer-based system. The electrical resistivity properties of the suitable oils at a common operating temperature are stored in the computer system. The actual resistivity history of the current oil at a like temperature is maintained as it is used and its volume in the sump is periodically determined. This stored information is used when it is time to add new makeup or replenishing oil to the existing oil or time to drain the existing oil from the sump and replace it with unused oil. This stored information and the method of this invention are used to determine whether the new oil is suitable for use in the engine or other lubricated mechanism.

The respective volumes of retained used oil and of new oil are determined. The last value of the resistivity of the used oil and the resistivity of the new mixture are obtained. As described in detail below these volumes and resistivity values are used to compare resistivity data for the added oil with like data, stored in the computer data base, for suitable lubrication oil. If the data for the added oil does not match stored data for good oils, the operator of the vehicle of other mechanism is alerted by the on-board system.

Much of the further discussion will detail the application of this technique to identify engine oil additions made to an engine in a motor vehicle. However, it will be readily appreciated that the same general procedure may be employed to characterize engine oil additions in other engine applications such as generators, engines used in marine or aerospace applications, and even oils used for primarily non-lubricious applications such as hydraulic systems.

Lubricating oil used in internal combustion engines is a complex mixture of components historically based on a petroleum hydrocarbon base stock derived from crude oil, with additives to improve certain properties. Increasingly, however, synthetic base stocks such as polyalphaolefin (PAO) or synthetic esters and related synthetics such as alkylated napthalenes and alkylated benzenes are used.

In an internal combustion engine, these engine oils are subject to severe operating conditions and will deteriorate with use. It has been recognized that different engines and operating conditions will result in greater and lesser rates of deterioration of a specific oil. Thus a number of national and international agencies have formulated standards for engine oils which reflect their resistance to deterioration in use and thus their suitability for specific applications. These agencies include the American Petroleum Institute (API), the International Lubricant Standardization and Approval Committee (ILSAC), ACEA (Association des Constructeurs Européens d'Automobiles) and the Japanese Automotive Standards Organization (JASO) as well as individual vehicle manufacturers.

In turn, vehicle manufacturers select the specifications that will meet their requirements for lubricant performance and service life. These requirements are met by the first lubricant fill of the engine by the original vehicle manufacturer, who has capability of specifying and monitoring the quality of the fluids charged during vehicle build. However subsequent oil charges are not necessarily as well controlled and, since differences between engine oils are not always apparent to either a vehicle operator or to vehicle mechanics and technicians, it is possible for an improper or lower grade lubricant to be used.

While the consequences of application of a higher than manufacturer-specified oil grade are expected to be benign, substitution of a lower-than-manufacturer-specified grade could potentially result in engine damage. It is therefore desirable to develop a capability to identify the nature of any oil additions made to an engine so that if a lower-than-manufacturer-specified grade has been used, appropriate corrective action may be taken.

It is also desirable that the nature of the added oil be determined after it has been charged. This both offers the opportunity to take advantage of on-board instrumentation which may be useful for other purposes, and places no restriction on where a vehicle owner may obtain unused replacement or make-up oil. However, it complicates the assessment of the added oil quality, since only the characteristics of the mixed and commingled used and unused oils will be measured. Thus the effect of the unused oil will be diluted by the residual used oil so that only composite measures will be determined and appropriate data processing will be required to extract the measures attributable to the unused oil from the composite measure.

The approach is based on on-board electrical measures of oil, specifically its resistivity, which exhibits both a characteristic initial value and characteristic evolutionary trends for specific oil formulations. Oils of known characteristics will be tested to establish both the initial and the evolutionary behavior of their resistivity. Since these are specific to a given oil, they will constitute a characteristic signature for a particular oil formulation. These data may then be collected and stored, for example as a look-up table in a computer storage device, where they may be accessed and compared with comparable data gathered from unknown oils. With increasing testing of known oils, a comprehensive data collection representative of the behavior of all tested oils will be developed.

Thus the resistivity changes of an unknown oil during use may be monitored for a period of time appropriate to record sufficient recognizable and characteristic features of the evolutionary profile which may be compared to the stored behaviors of known oils. When the behaviors of the unknown oil and a specific known oil are judged to be substantially identical, the unknown oil formulation will be judged identical to the formulation of the known oil.

SUMMARY OF THE INVENTION

This invention describes a means of identifying the quality of an oil, particularly the quality of an unused oil added to a pre-existing volume of used oil from measurements of the resistivity of the resultant oil mixture.

The practice of this invention may be used to assess the formulation of oil additions in virtually any engine or mechanism where oil loss or degradation of oil properties requires periodic oil additions. The most immediate application is to internal combustion engines, particularly those used in motor vehicles, but also including those used in stationary, marine or aerospace applications. However, the invention has broad utility and can find wider application, for example in assessing the quality of make-up fluid in hydraulic systems.

Lubricant oils in internal combustion engines may exhibit a multiplicity of formulations differing in both base oil characteristics and additive package. The electrical impedance, and hence the resistivity and permittivity of these oils may be evaluated using instrumentation, measurement and analysis procedures well known to those skilled in the art and described, for example, in U.S. Pat. No. 7,362,110, Halalay et al., U.S. Pat. No. 6,922,064 Halalay et al. and U.S. Pat. No. 7,370,514, Halalay et al.

These derived assessments of resistivity may be monitored frequently enough that a near-continuous record of the variation of these characteristics may be developed. Further, this record may be stored, for example in a computer or similar device, and form one of a set of reference data characteristic of particular lubricating oils. The variation of resistivity during use of an unknown oil may then be compared with a library of reference data gathered for a large number of known lubricating oils to locate a set of reference data which exhibits substantially the same behavior as the unknown oil. When such a substantial match is achieved, the unknown lubricating oil will be presumed to possess a formulation substantially identical to that of the matched reference formulation.

The nature of the base oil and the additive package determines the initial resistivity of the oil and the evolution of the resistivity of the oil during use which is related to the deterioration of the oil during use. Hence, the suitability of an unknown lubricating oil for a particular application may be determined by knowledge of its formulation, which, in turn, conveys characteristic, measurable electrical characteristics to the oil.

Turning to a specific implementation in a motor vehicle, there are three situations where oil identification is desired:
  on initial oil fill
  on oil change
  on oil replenishment These three cases represent situations where the oil, after addition of unused oil comprises, exclusively unused oil, substantially unused oil and substantially used oil. In all cases, an initial identification of the unused oil will be made based on assessment of its initial resistivity and the initial assessment refined using the time evolution of the resistivity of the unused oil during vehicle use. It will be appreciated, however that for cases (b) and (c) where the unused oil will be commingled with used oil, resistivity measurements will reflect the behavior of the commingled oils. Thus, for these cases additional data processing is required to extract the resistivity characteristic of the unused oil.

Specifically the composite signature which results from the intermixed and commingled used and unused oils must be decomposed to yield time-varying values of resistivity attributable to each of the constituents. This may be accomplished through application of the following steps:

(a) measure the electrical resistivity of a vehicle lubricant during use through an on-vehicle sensor and construct its time dependence;

(b) determining the remaining volume of vehicle oil just prior to oil replacement or replenishment using an on-vehicle engine oil level sensor;

(c) determine the new total oil volume after addition of the unused oil, again using the on-vehicle oil level sensor;

(d) record the time when the addition of the unused oil occurred;

(e) determine the volume of unused oil added by difference between the volumes measured in steps (b) and (c) and thereby compute the volumetric proportion of used and unused oil;

(f) measure the electrical resistivity of the mixture of used and unused oils using an on-vehicle sensor;

(g) calculate the resistivity of the added unused oil from a knowledge of the resistivity of the used oil immediately before the oil addition, the resistivity of the mixture of used and fresh oil immediately after the addition and the volume fractions of the used and added oil, using a mixing rule for the electrical resistivity;

(h) continue to measure the resistivity of the oil mixture with continued use to develop a near-continuous record of resistivity versus time; and (i) identify the time from the oil addition at which a peak in the resistivity versus time curve is observed.

With the further step of comparing the resistivity characteristic of the unused oil against a library of resistivity characteristics of known oils, the unused oil may be identified and its conformance to manufacturer specifications and thus its suitability for the application determined.

In a vehicular application, the control electronics of the vehicle may be programmed so that a warning is issued to the user if the added oil is out-of-specification.

DESCRIPTION OF PREFERRED EMBODIMENTS

This invention is a method for determining the quality of lubrication oil added to a quantity of used oil in an operating engine or mechanism. The method is described with specific application to an internal combustion engine mounted in a vehicle and contemplates the use of a suitable lubricating oil flow-through electrical sensor for monitoring the electrical resistivity of the oil at a normal operating temperature and while in use in an engine or other operating mechanism. The practice of the method is supported by suitable electronic instrumentation.

An example of a suitable cell for measurement or determination of resistivity and permittivity values of an engine oil or other liquid is disclosed in U.S. Pat. No. 7,362,110, "Measurement Cell for Liquids," Halalay et al. and is incorporated into this specification to illustrate the design and use of such a cell. A method of using such a cell in determining and using resistivity values and permittivity values of an engine oil is disclosed in U.S. Pat. No. 7,370,514, "Determining Quality of Oil in Use," Halalay et al. and is likewise incorporated into this specification to further illustrate the measurement and use of electrical properties in projecting the useful life of a lubrication oil in an operating engine. Another example of a method of using impedance instrumentation to monitor resistivity of a fluid in a reservoir is disclosed in U.S. Pat. No. 6,922,064, "Fluid Quality Test Method Based on Impedance," Halalay et al.

Data supportive of the present invention are shown in FIGS. 1-6.

Figure 1:
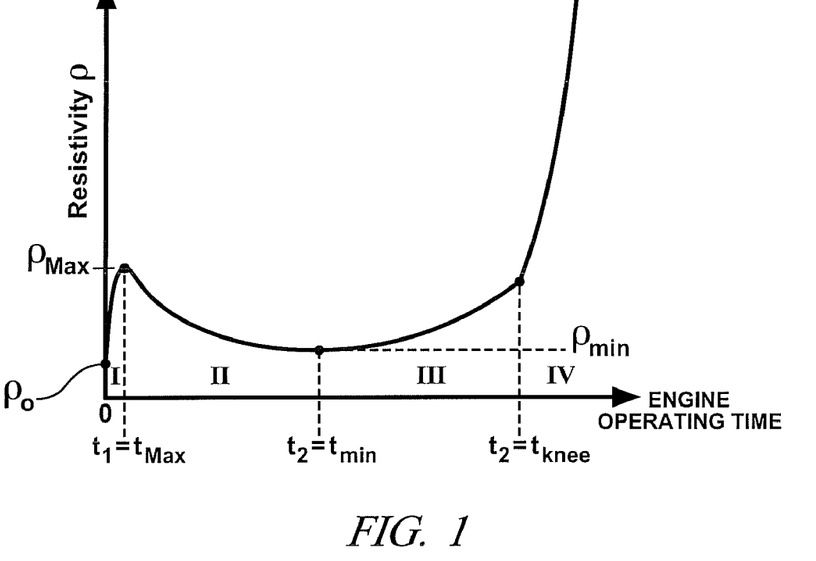
FIG. 1 shows a curve characteristic of the variation of engine oil resistivity with time of use and displays features characteristic of oil resistivity measurements during use. Specifically note the initial resistivity $\rho_0$, and the peak resistivity $\rho_{max}$ occurring at engine operating time $t_{max}$ and marking the boundary between Region I and Region II in the figure. Additional features which may be observed on the curve are designated as Region II and Region IV respectively
Figure 2:
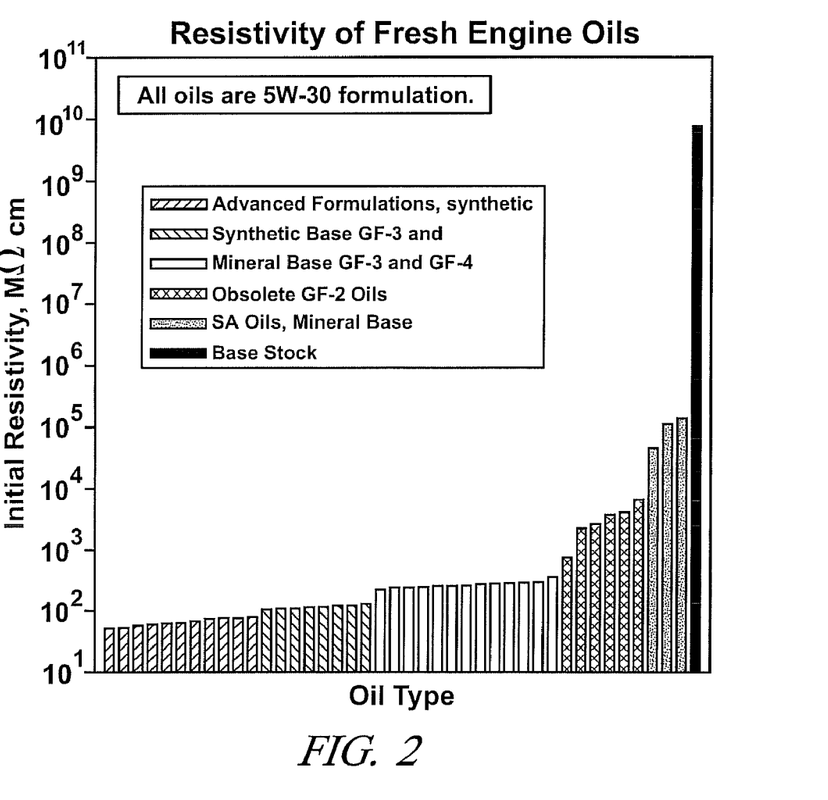
FIG. 2 shows a bar graph which identifies the magnitude of the initial resistivity with classes of oil formulations identified with ILSAC and API designations for a variety of formulated oils.
Figure 3:
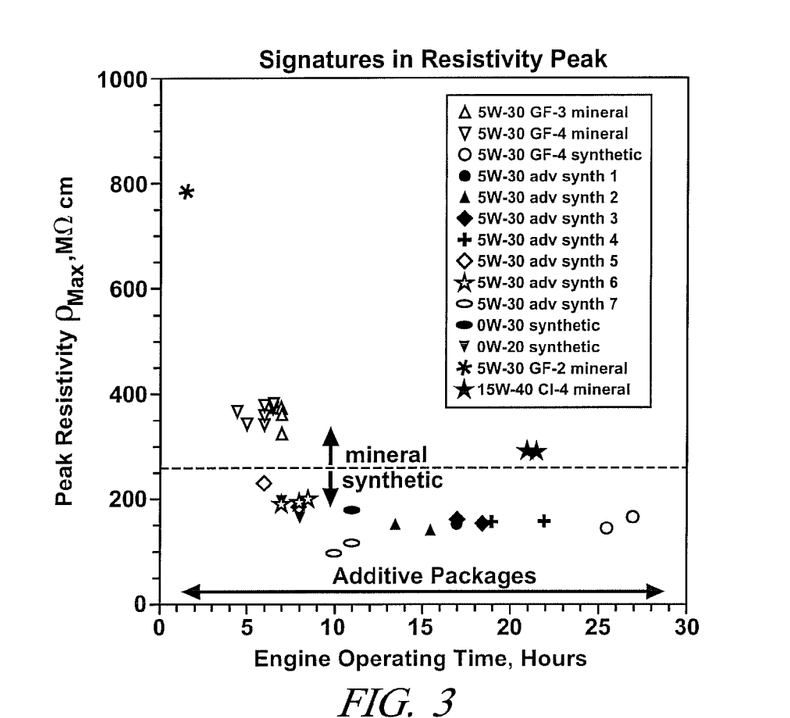
FIG. 3 shows data representative of the influence of various oil base stocks and additive packages on the maximum resistivity measured at the initial resistivity peak such as is shown as $\rho_{max}$ in FIG. 1 and the engine operating time, $t_{max}$, after an oil change at which this peak is observed.

FIG. 1 is an example of a typical curve showing the change in resistivity of a particular engine oil with engine operating time obtained though on-vehicle measurement and analysis devices. Of particular interest is that FIG. 1 shows a peak at short engine operating times. This feature appears to be a universal feature of such resistivity-engine operating time curves and is the basis for one of the procedures for identification of additive oil to be described further below. FIG. 2 shows a compilation of resistivity data gathered on a number of unused engine oils of differing base chemistry and with differing quantities and combinations of additives. FIG. 3 illustrates that the peak resistivity i.e. the maximum of the resistivity-engine operating time curve early in an engine oil's usage varies with base oil formulation and that the engine operating time at which this peak is observed varies with the type of additive package. FIG. 3 focuses on the influence of base oil formulation and additive package. It clearly shows that, while different oil families corresponding to different API and ILSAC classifications demonstrate similar maximum values of the resistivity for the same type of base oil (i.e. mineral vs. synthetic), the timing of the peak is sensitive to, and can distinguish between, various additive packages.

Figure 4:
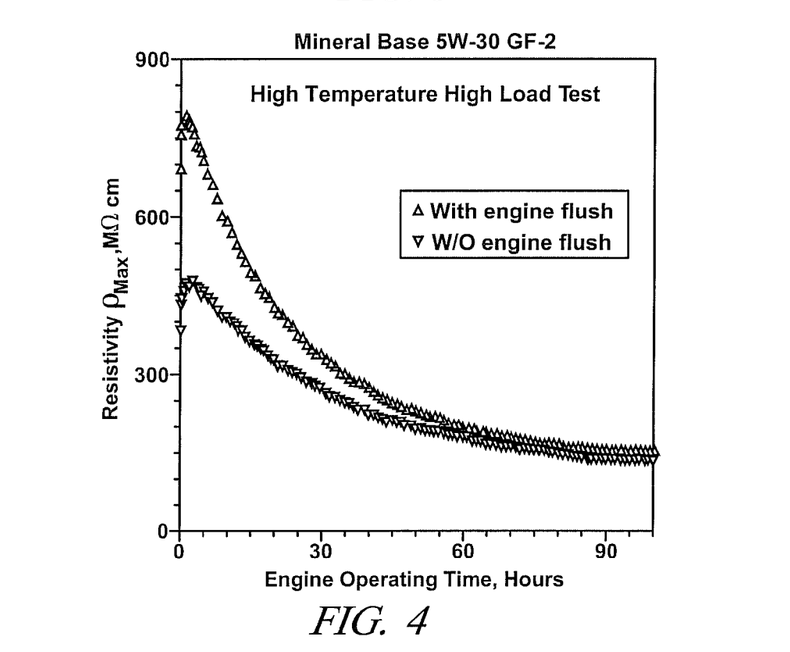
FIG. 4 is a resistivity versus engine operating time plot for a specific engine oil following an oil change involving flushing all used oil from the system, designated as "With engine flush", and a second oil change in which new, unused oil was added to an engine nominally drained of used oil, designated as "W/O engine flush".

To appreciate the complexity of the problem it is only necessary to review FIG. 4 which shows the resistivity versus engine operating time behavior of a substantially-unused oil for two situations. In both cases the engine oil at end of life has been replaced with new unused oil. However in one case (with engine flush), the used oil was drained; unused replacement oil was added; the replacement oil was then drained; and a second charge of unused replacement oil was added. In the second case (without engine flush, designated as W/O engine flush), the used oil was simply drained and replaced with unused replacement oil. A clear difference in behavior in these two cases is observed.

When the oil is replaced in the manner described as 'With engine flush', the behavior expected for unused oil i.e. a resistivity peak of ~800 MΩcm is observed. When the oil is replaced in the manner described as 'W/O engine flush', a resistivity peak of ~480 MΩcm is observed. Differences in similar ratio are also observed in the initial resistivity. Thus the effect of even a small quantity of used oil retained in the lubricating system after the used oil has been drained is significant inasmuch as it has changed both the peak height and the initial resistivity by almost a factor of 2. Note, however, that the timing of the resistivity peak is essentially unchanged in the two data sets.

Fortunately, as FIG. 2 makes clear, the resistivity for fresh various oil formulations, ranging from fully formulated synthetic based GF-4 oils to base stock, spans 7 orders of magnitude (i.e. a factor of 10 million). Such a variation on a logarithmic scale makes an "out-of-specification" warning still possible, in spite of a variation by a factor of 2, as discussed with reference to FIG. 4.

Furthermore, see FIG. 3, the peak resistivity and engine operating time to resistivity peak provide additional information on the engine oil: the nature of the additive package correlates well with the engine operating time at which the resistivity peak is observed, while the value of the resistivity at the local maximum correlates with the base oil characteristics. Hence the oil characteristics may be inferred and compared with the manufacturer's requirements.

Figure 5:
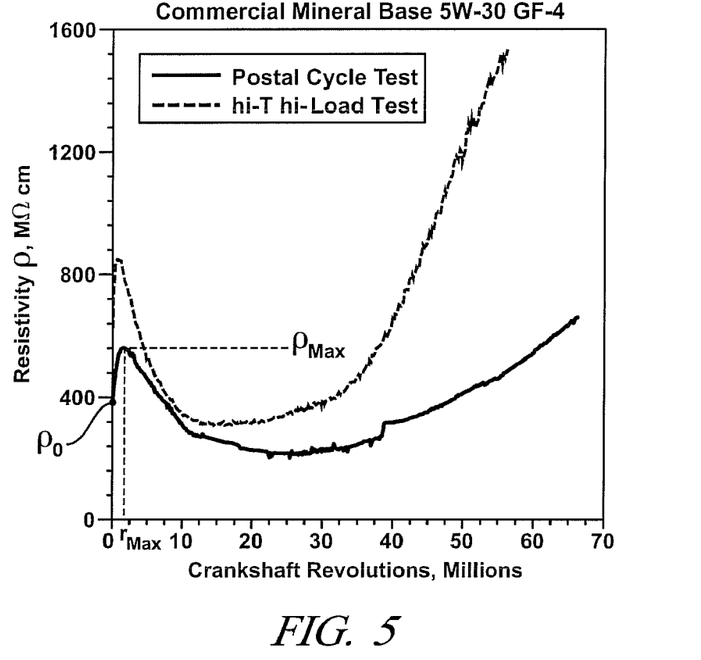
FIG. 5 is a resistivity versus Crankshaft Revolutions plot for a mineral base GF-4 engine oil during two dynamometer tests with widely different operating parameters: a high-temperature high-load (HTHL) test approximating steady-state high speed driving through a desert while towing a trailer; and, a milder test employing frequent starting, acceleration, and deceleration (PC or "postal cycle" test).
Figure 6:
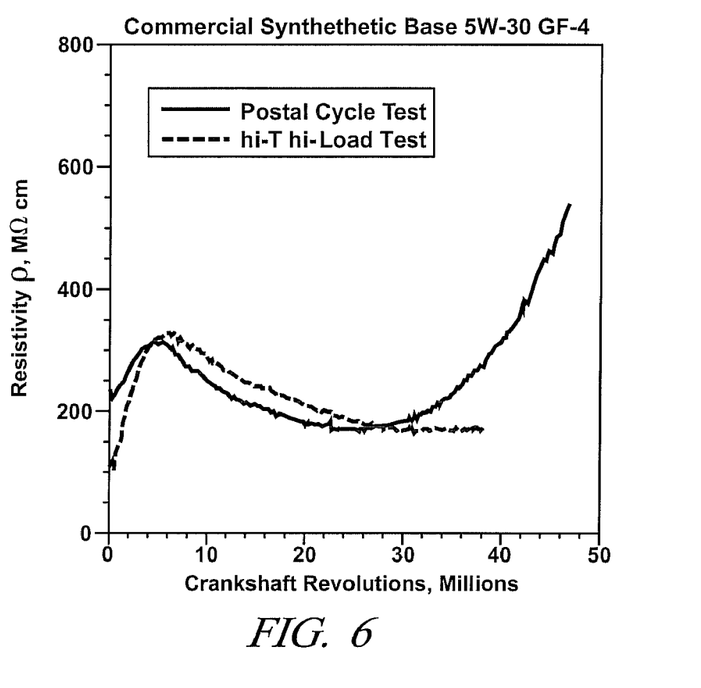
FIG. 6 is a resistivity versus Crankshaft Revolutions plot for a synthetic base GF-4 engine oil during an HTHL and a PC test.

The robustness of the signatures in the resistivity peak to driving conditions is addressed in FIGS. 5 and 6. FIGS. 5 and 6 display the test results respectively for mineral base and synthetic base GF-4 engine oils as a function of number of engine revolutions during two dynamometer tests with widely different operating parameters: (i) a high-temperature high-load test approximating high speed driving through a desert while towing a trailer and (ii) a milder test under conditions approximating frequent starting, acceleration, deceleration and stopping. The data in FIGS. 5 and 6 were plotted as a function of number of engine revolutions instead of engine operating time, since the plots represent data from tests with different test conditions, and in particular different of engine speeds (i.e. revolutions per minute). As examination of FIGS. 5 and 6 immediately shows, the occurrence of the resistivity peak at early numbers of crankshaft revolutions is largely independent of test conditions, and thus provides the robustness needed for an unambiguous identification of an engine oil during service.

The detailed method comprises:

(a) measuring the electrical properties, at least the resistivity of the oil, of a wide range of lubricating oils under standardized test procedures over the useful life of the oil wherein at least one of the standard test procedures requires measuring the electrical properties at a substantially fixed reference temperature in excess of 90° C.; generating a near-continuous curve of the variation in resistivity of the oil with engine operating time in sufficient detail that at least the initial resistivity $\rho_0$ and the time, $t_{Max}$, at which the resistivity peak, $\rho_{Max}$, shown in FIG. 1, may be identified; associate at least the initial resistivity $\rho_0$, the maximum resistivity $\rho_{max}$ and the engine operating time $t_{Max}$ characteristic of the resistivity peak with the specific oil under test and store these characteristics in some retrievable form, for example in a look-up table in an electronic computer.

(b) measuring the electrical properties of the vehicle lubricant during use in a vehicle through an on-vehicle sensor and extracting the oil's resistivity as a function of engine operating time, making measurements sufficiently frequently to generate a near-continuous record of resistivity versus engine operating time such as is shown in FIG. 1. This procedure, well known to those skilled in the art has been documented in the Halalay et al. '514 patent and comprises: circulating oil through an appropriate sensor; making repeated measures of the impedance of the oil at a near-constant temperature in excess of 90° C.; extracting from the impedance measures the oil resistivity; and generating a curve of resistivity versus engine operating time.

(c) determining the remaining quantity of vehicle oil just prior to oil replacement or replenishment using an on-vehicle engine oil level sensor capable of providing a signal whose magnitude is proportional to the volume of oil present.

(d) determining the new total oil volume after addition of the unused oil, again using the on-vehicle oil level sensor;

(e) recording the time when the addition of the unused oil occurred;

(f) determining the volume of unused oil added by difference between the volumes measured in steps (d) and (c) and thereby computing the volumetric proportion of used and unused oil;

(g) measuring the electrical resistivity of the mixture of used and unused oils using an on-vehicle sensor;

(h) calculating the resistivity of the added unused oil, which corresponds to the initial resistivity $\rho_0$ of the unused oil, from a knowledge of the resistivity of the used oil immediately before the oil addition, the resistivity of the mixture of used and fresh oil immediately after the addition and the volume fractions of the used and added oil, using a mixing rule for the electrical resistivity;

(i) comparing the value of the initial resistivity of the added unused oil with the values in a look-up table with initial resistivity measurements recorded for a wide variety of unused oils and so enable preliminary identification of the added oil;

(j) continuing to measure the resistivity of the oil mixture with continued use to develop a near-continuous record of resistivity versus engine operating time;

(k) identifying the engine operating time (measured from the engine operating time of the oil addition) at which a peak in the resistivity versus engine operating time curve is observed, $t_{Max}^*$; This may be accomplished by: appropriately smoothing the curve to minimize the influence of noise such as by computing a multi-point running average; taking derivatives of the curve; and identifying the time at which the derivative assumes a value of zero as it smoothly changes from positive to negative as the time of the resistivity peak. An alternative and simpler procedure is to smooth the curve, again a multipoint running average would be suitable; continually track the averaged value of the resistivity with time and note whether, from time interval to time interval, its value was increasing or decreasing; and identify the point at which the resistivity after exhibiting an initial rise began to decline as the time of the resistivity peak;

(l) referring to the stored data representative of the behavior of known oils as described in step (a), compare the engine operating time (relative to the moment of oil change) of resistivity peak just identified for the oil mixture with the resistivity peaks for the known oils until a known oil is found whose resistivity peak occurs at a substantially identical engine operating time to the resistivity peak just determined and representative of the unknown oil. Identify the unknown oil with this known oil.

The nature of the added unused oil is identified at two stages in this procedure—at step (i) and at step (l). From review of FIG. 2, it is clear that the preliminary assessment of oil quality enabled at step (i) is directed primarily to determining the general class of oils rather than toward identifying a specific oil formulation. By contrast the identification at step (l), as FIG. 3 makes clear, enables much greater discrimination. Ideally these two determinations should agree but if, due to the greater discrimination of the resistivity peak/engine operating time peak they lead to conflicting assessments of oil suitability the last-determined identification is accepted.

If either measure indicates that the added oil does not meet specifications, it is intended that a warning or series of increasingly urgent warnings will be conveyed to the vehicle operator. This may be done by means well known to those skilled in the art and will inform the operator that the oil should be changed immediately. Thus a warning issued at step (i) will truncate the procedure at that point and a warning issued at step (l) will over-ride any failure to warn at step (i).

Referring back to the three situations identified earlier i.e. an initial oil fill, an oil change, and oil replenishment, it is clear that the above procedure is inclusive enough to address these three cases. In the case of an oil replenishment all the listed steps are required; in the case of an initial oil fill, only steps (a), (b), (i) and (l) should be followed.

In the case of an oil change, two procedures are possible, depending on whether the quantity of residual oil remaining in the engine can be reliably measured. If the quantity of residual oil can be measured, this situation may be treated as an oil addition and all steps should be followed. If the quantity of residual oil cannot be reliably measured then this situation resembles the initial oil fill situation and only steps (a), (b), (i) and (l) should be followed.

The above procedure should enable identification of the unknown oil in cases where sufficient unused oil is added that its effects on the resistivity of the oil mixture are not swamped by the effects of a much greater volume of used oil. In some cases however the volume of oil added may be so small that the resistivity peak associated with the oil addition cannot be discerned against the background resistivity attributable to the much larger volume of used oil.

A more significant issue arises when the electrical measurements are subject to significant noise. If the resistivity peak is small and barely detectable, as in the case above, noise could be interpreted by the system as a peak generating an erroneous identification of the oil addition and possibly prompting unnecessary action by the vehicle operator.

To guard against this situation, implementation of the algorithm will be conditioned on the volumetric proportion of new oil determined at step (f) exceeding a pre-set threshold. Thus if less than a minimum quantity of oil is added the algorithm will not be implemented and no attempt will be made to identify the oil addition. Simple scaling of the resistivity peaks shown in FIGS. 1, 4, 5 and 6 indicates that even if the peak height were reduced by 20% it should still be discernible against the more slowly varying background and rapidly varying noise. Hence a ratio of unused to used oil of 0.2 or greater will be considered to yield accurate results. Since, typically, users will add oil in one quart increments, corresponding to a ratio of unused to used oil of approximately 0.25 for a 5 quart sump, most oil additions should exceed this threshold.

A second case which should be considered is one in which an oil addition is required before the used oil has been in use for long enough to develop its resistivity peak. In this case there is no way to differentiate the used oil peak from the unused oil peak and no engine oil identification can be performed.

Finally note that the higher the quality of the oil, the longer the time to reach the resistivity peak. Thus, low grade oils which have the greatest potential to harm an engine will be detected very early in service when they will have had the least opportunity to cause damage while the higher grade oils, which will have the least potential for engine damage will be detected later.

The procedure described above is suitable for engines which undergo relatively fixed duty cycles or those which undergo repetitive duty cycles of relatively short duration. For example marine or stationary applications. For engines which experience varying duty cycles, especially varying duty cycles of long duration, a time based identification of the resistivity peak might confuse oil identification. This can occur, using operation in a motor vehicle as an example, because the oil degradation experienced under 30 hours of use at 30 miles per hour will not be the same as the oil degradation experienced under 30 hours of use at 65 miles per hour. However as FIGS. 5 and 6 make clear, good correspondence of the resistivity peaks even under radically different driving schedules is achieved if the index for the evolution of degradation is crankshaft revolutions rather than time. Thus a yet further embodiment of the invention comprises the detailed method of:

(a) counting the number of engine crankshaft revolutions and measuring the electrical properties, at least the resistivity of the oil, of a wide range of lubricating oils under standardized test procedures over the useful life of the oil wherein at least one of the standard test procedures requires measuring the electrical properties at a substantially fixed reference temperature in excess of 90° C.; generating a near-continuous curve of the variation in resistivity of the oil with engine crankshaft revolutions in sufficient detail that least the initial resistivity ($\rho_0$), and at least the number of crankshaft revolutions ($r_{Max}$) characteristic of the resistivity peak ($\rho_{Max}$), shown in FIG. 5, may be identified; associate at least $\rho_0$, $\rho_{Max}$ and $r_{Max}$ with the specific oil under test and store these characteristics in some retrievable form, for example in a look-up table in an electronic computer.

(b) measuring the electrical properties of the vehicle lubricant during use in a vehicle through an on-vehicle sensor and extract the oil's resistivity as a function of engine crankshaft revolutions, making measurements sufficiently frequently to generate a near-continuous record of resistivity versus engine crankshaft revolutions. This procedure, well known to those skilled in the art has been documented in the Halalay et al. '514 patent and comprises: circulating oil through an appropriate sensor; making repeated and simultaneous measures of the impedance of the oil at a near-constant temperature in excess of 90° C. and the engine crankshaft revolutions; extracting from the impedance measures the oil resistivity; and generating a curve of resistivity versus engine crankshaft revolutions.

(c) determining the remaining quantity of vehicle oil just prior to oil replacement or replenishment using an on-vehicle engine oil level sensor capable of providing a signal whose magnitude is proportional to the volume of oil present.

(d) determining the new total oil volume after addition of the unused oil, again using the on-vehicle oil level sensor;

(e) recording the engine crankshaft revolutions when the addition of the unused oil occurred;

(f) determining the volume of unused oil added by difference between the volumes measured in steps (d) and (c) and thereby compute the volumetric proportion of used and unused oil;

(g) measuring the electrical resistivity of the mixture of used and unused oils using an on-vehicle sensor;

(h) calculating the resistivity of the added unused oil from a knowledge of the resistivity of the used oil immediately before the oil addition, the resistivity of the mixture of used and fresh oil immediately after the addition and the volume fractions of the used and added oil, using a mixing rule for the electrical resistivity;

(i) comparing the value of the resistivity of the added unused oil with the values in a look-up table with the resistivity of a wide variety of unused oils and so determine the identity of the added oil;

(j) continuing to measure the resistivity of the oil mixture with continued use to develop a near-continuous record of resistivity versus time;

(k) identifying the number of engine crankshaft revolutions (since the oil addition) at which a peak in the resistivity versus time curve is observed, $r_{Max}^*$; this may be accomplished by: appropriately smoothing the curve to minimize the influence of noise such as by computing a multi-point running average; taking derivatives of the curve; and identifying the time at which the derivative assumes a value of zero as it smoothly changes from positive to negative as the time of the resistivity peak. An alternative and simpler procedure is to smooth the curve, again a multipoint running average would be suitable; continually track the averaged value of the resistivity with engine crankshaft revolutions and note whether, from engine crankshaft revolutions interval to engine crankshaft revolutions interval, its value was increasing or decreasing; and identify the point at which the resistivity after exhibiting an initial rise began to decline as the engine crankshaft revolutions of the resistivity peak;

(l) referring to the stored data representative of the behavior of known oils as described in step a. compare the engine crankshaft revolutions (relative to the oil change) of the resistivity peal just identified for the oil mixture with the resistivity peaks for the known oils until a known oil is found whose resistivity peak occurs at substantially identical engine crankshaft revolutions to the resistivity peak just determined and representative of the unknown oil. Identify the unknown oil with this known oil.

Clearly the previously-discussed issues of the relative oil volumes and the prior occurrence of a resistivity peak would also apply in this embodiment. Also the application all steps of the method or of only selected steps (a), (b), (i) and (l) of the method for the cases of initial oil fill, oil replenishment or oil replacement follows the pattern developed in discussion of the previous embodiment.

This invention has been described in terms of specific embodiments directed to its application to an internal combustion engine in a vehicle. However the influences of oil formulation on oil resistivity and the evolution of oil resistivity during use have been described in sufficient detail to enable one skilled in the art to apply this invention to alternate engines and mechanisms.

Accordingly the scope of this invention is limited only by the following claims.

The invention claimed is:

1. A method of identifying a replenishing oil when a first volume of replenishing oil is mixed with a second volume of used oil to create a volume of mixed oil, comprising:
   measuring the electrical resistivity of the used oil prior to replenishment;
   measuring the electrical resistivity of the mixed oil;
   computing the resistivity of the replenishing oil; and
   comparing the resistivity of the replenishing oil with known resistivities of
   candidate replenishing oils until a candidate oil with a resistivity suitably
   correspondent with the resistivity of the replenishing oil is identified.

2. The method of claim 1 wherein the used oil comprises an oil used in a hydrocarbon-fueled engine.

3. The method of claim 2 wherein;
   the engine is in a vehicle;
   the electrical resistivity measurements are made on the vehicle using an on-vehicle sensor;
   the computation of oil resistivity is conducted using an on-vehicle computing engine; and
   the comparison of the resistivities of the replenishing oil with the known resistivities of candidate replenishing oils is conducted using an on-vehicle computing engine.

4. A method of identifying a replenishing oil when a first volume of replenishing oil is mixed with a second volume of used oil to create a volume of mixed oil, comprising:
   measuring the electrical resistivity of the used oil;
   measuring the second volume;
   determining the first volume;
   measuring the electrical resistivity of the oil mixture;
   using an appropriate mixture rule and knowledge of the first and second volumes to compute the resistivity of the first oil; and
   comparing the resistivity of the replenishing oil with known resistivities of candidate replenishing oils until a candidate oil with a resistivity suitably correspondent with the resistivity of the replenishing oil is identified.

5. The method of claim 4 wherein the used oil comprises an oil used in a hydrocarbon-fuelled engine.

6. The method of claim 5 wherein:
   the engine is in a vehicle;
   the electrical resistivity measurements are made on the vehicle using an on-vehicle sensor;
   the computation of oil resistivity is conducted using an on-vehicle computing engine; and
   the comparison of the resistivities of the replenishing oil with the known resistivities of candidate replenishing oils is conducted using an on-vehicle computing engine.

7. The method of claim 4 wherein the measurement of the first volume is made using an on-vehicle oil level sensor.

8. The method of claim 4 wherein the determination of the first volume comprises the method of;
   measuring the volume of the oil mixture using an on-vehicle oil level sensor;
   subtracting the volume of the measured second volume of used oil from the measured oil mixture volume to compute a remainder and;
   identifying the remainder with the first volume.

9. A method of identifying a first unused oil present in an oil mixture comprising a first volume of a first unused oil and a second volume of a second used oil comprising;
   storing data on oil resistivity for some number of reference unused oils in a retrievable manner;
   measuring the electrical resistivity of the second oil;
   measuring the second volume;
   determining the first volume;
   measuring the electrical resistivity of the oil mixture;
   using an appropriate mixture rule and knowledge of the first and second volumes to compute the resistivity of the first oil and;
   identifying the first unused oil through substantially matching the resistivity of the first oil with the resistivity of a one of the reference unused oils.

10. The method of claim 9 wherein the used oil comprises oil used in an engine in a vehicle.

11. The method of claim 10 wherein;
    the electrical resistivity measurements are made using an on-vehicle sensor;
    measurement of the second volume is made using an on-vehicle oil level sensor;
    the determination of the first volume comprises the method of; measuring the volume of the oil mixture using an on-vehicle oil level sensor; subtracting the volume of the measured second volume of used oil from the measured oil mixture volume to compute a remainder; and identifying the remainder with the first volume.

12. The method of claim 11 wherein the identification of the first oil is made on the vehicle.

13. A method of identifying a first unused oil present in an oil mixture in an engine generated by addition of a first volume of a first unused oil and a second volume of a second oil comprising;
    storing data, in a retrievable manner, on the variation of oil resistivity with engine operating time, measured under specified engine operating conditions, during use in an operating engine for some number of reference oils;
    measuring the variation of electrical resistivity of the second oil with engine operating time and extracting the engine operating time corresponding to the time, $t_{Max}$ at which the variation of resistivity with engine operating time exhibits a maximum;
    measuring the second volume of the second oil;
    determining the first volume of the first oil;
    recording the engine operating time at which the first volume is added to the second volume as a reference time;
    repeatedly measuring, under specified engine operating conditions, the variation of the electrical resistivity of the oil mixture with engine operating time, during use in an operating engine where the time is measured from the reference time with sufficient frequency to generate a near-continuous record of resistivity with engine operating time;
    extracting from the near-continuous record of resistivity with engine operating time a time interval $t_{Max}$* from the reference time at which the resistivity of the oil mixture exhibits a maximum;
    attributing the time $t_{Max}$* at which the oil mixture exhibits a peak in its resistivity with engine operating time to the first unused oil and;
    through substantially matching the time $t_{Max}$* with the time to peak resistivity of one of the reference unused oils and identifying the first unused oil with the one of the reference unused oils.

14. The method of claim 13 wherein the specified engine operating conditions comprise a temperature exceeding 90° C.

15. The method of claim 13 wherein the determination of the first volume comprises the method of;
    measuring the volume of the oil mixture using an on-vehicle oil level sensor;

subtracting the volume of the measured second volume of used oil from the measured oil mixture volume to compute a remainder and;

identifying the remainder with the first volume.

16. The method of claim 13 wherein the process of identification of the first unused oil is terminated if the ratio of the first volume to the second volume does not exceed a predetermined value.

17. The method of claim 13 wherein the process of identification of the first unused oil is terminated if no resistivity maximum with engine operating time, $t_{Max}$, has been determined for the second oil.

18. A method of identifying a first unused oil present in an oil mixture in an engine generated by addition of a first volume of a first unused oil and a second volume of a second oil comprising;

storing data, in a retrievable manner, on the variation of oil resistivity with engine crankshaft revolutions, measured under specified engine operating conditions, during use in an operating engine for some number of reference oils;

measuring the variation of electrical resistivity of the second oil with engine crankshaft revolutions and extracting the engine crankshaft revolutions corresponding to the count, $r_{Max}$ at which the variation of resistivity with engine crankshaft revolutions exhibits a maximum;

measuring the second volume of the second oil;

determining the first volume of the first oil;

recording the engine crankshaft revolutions at which the first volume is added to the second volume as a reference crankshaft revolution count;

repeatedly measuring, under specified engine operating conditions, the variation of the electrical resistivity of the oil mixture with engine crankshaft revolutions, during use in an operating engine where engine crankshaft revolutions are measured from the reference engine crankcase revolution with sufficient frequency to generate a near-continuous record of resistivity with engine crankshaft revolutions;

extracting from the near-continuous record of resistivity with engine crankshaft revolutions a count $r_{Max}^*$ from the reference crankshaft revolution count at which the resistivity of the oil mixture exhibits a maximum;

attributing the value $r_{Max}^*$ at which the oil mixture exhibits a peak in its resistivity with engine crankshaft revolutions to the first unused oil and;

through substantially matching the engine crankshaft revolutions $r_{Max}^*$ with the engine crankshaft revolutions to peak resistivity of one of the reference unused oils, identifying the first unused oil with the one of the reference unused oils.

19. The method of claim 18 wherein the specified engine operating conditions comprise a temperature exceeding 90° C.

20. The method of claim 18 wherein the determination of the first volume comprises the method of;

measuring the volume of the oil mixture using an on-vehicle oil level sensor;

subtracting the volume of the measured second volume of used oil from the measured oil mixture volume to compute a remainder and;

identifying the remainder with the first volume.

21. The method of claim 18 wherein the process of identification of the first unused oil is terminated if the ratio of the first volume to the second volume does not exceed a predetermined value.

22. The method of claim 18 wherein the predetermined value is 0.2.

23. The method of claim 18 wherein the process of identification of the first unused oil is terminated if no resistivity maximum with engine crankshaft revolutions, $r_{Max}$, has been determined for the second oil.

* * * * *